(12) United States Patent
McClaine

(10) Patent No.: US 6,615,844 B2
(45) Date of Patent: Sep. 9, 2003

(54) HAIR THINNING MEASUREMENT DEVICE

(75) Inventor: Elayne P. McClaine, Basking Ridge, NJ (US)

(73) Assignee: Pharmacia & Upjohn, Kalamazoo, MI (US)

(*) Notice: Subject to any disclaimer, the term of this patent is extended or adjusted under 35 U.S.C. 154(b) by 0 days.

(21) Appl. No.: 09/969,346

(22) Filed: Oct. 2, 2001

(65) Prior Publication Data

US 2003/0062057 A1 Apr. 3, 2003

(51) Int. Cl.[7] ............................................. A45D 24/34
(52) U.S. Cl. ......................... 132/200; 132/148; 33/101
(58) Field of Search .............................. 132/200, 148, 132/150; 33/101; D10/73

(56) References Cited

U.S. PATENT DOCUMENTS

| | | | | |
|---|---|---|---|---|
| 1,630,505 A | * | 5/1927 | Walther | 33/674 |
| 2,547,354 A | * | 4/1951 | Worden | 33/674 |
| 3,459,197 A | * | 8/1969 | Wilson | 132/148 |
| 4,062,120 A | * | 12/1977 | Lacagnina et al. | 33/166 |
| 4,416,063 A | * | 11/1983 | Nestor et al. | 33/163 |
| D274,414 S | * | 6/1984 | Audsley | D10/73 |
| 4,599,800 A | * | 7/1986 | Wyrwich et al. | 33/143 |
| 5,483,751 A | * | 1/1996 | Kodato | 33/811 |
| 6,253,771 B1 | * | 7/2001 | McClaine | 132/200 |

* cited by examiner

Primary Examiner—Kevin Shaver
Assistant Examiner—David C. Comstock
(74) Attorney, Agent, or Firm—Craig M. Bell

(57) ABSTRACT

A self-analysis hair density measuring device comprises a housing body with a calibrated gauge element movably affixed to one side of the housing body. There are at least two or preferably three movable pronged tines extending from within the proximal end of said housing body with a gear or pivot mechanism disposed within the housing body that operatively connects the tines with the gauge. There is also a flexible, handle extending from the distal end of the housing body that is numerically calibrated with a flexible, tapered distal tip. Using a minor, the tines may be used to measure the width of one's part which, over time, may indicate whether the part is widening or narrowing and thereby is directly indicative of the rate of hair loss and/or regrowth. The flexible handle is wrapped around the user's ponytail or mane and is directly indicative of hair density.

11 Claims, 1 Drawing Sheet

HAIR THINNING MEASUREMENT DEVICE

FIELD OF THE INVENTION

The present invention relates generally to methods and devices for treating hair loss and thinning. More specifically, the present invention relates to methods and means for determining the amount and/or rate of hair loss in a given female individual. More specifically, the invention pertains to a device that allows for the self-analysis of the density of one's hair and thereby determines the rate of hair loss or re-growth through therapy.

BACKGROUND OF THE INVENTION

Hair loss is a problem which many men and women experience in their lifetime. The most common cause of hair loss is associated with the normal aging process. The process of losing one's hair is most often gradual. It is usually first noticed during washing or grooming. This observation is imprecise in predicting permanent hair loss, as most individual hair follicles go into a dormant period (20% of the hair population at any one time) and a reduction of hair population may be partly the result of this process although this process is usually uniform.

The distinguishing factor which differentiates permanent hair loss from cyclical hair loss is that the population of the hair decreases gradually in affected areas resulting in a permanent loss of hair and a reduction of hair population and hair density. The permanent loss of hair is often selective by anatomical site. In men, hair loss follows one pattern ("male pattern baldness" or "androgenic alopecia") and in women it follows another pattern. The process of losing hair also occurs at different rates, for different periods of time and at different ages, even in the same individual.

Dermatologists recognize many different types of hair loss, the most common by far being "androgenic alopecia" wherein human males begin losing scalp hair at the temples and on the crown of the head in early adult life. This type of hair loss is more common and more severe in males, hence its common name "male pattern baldness." However, similar patterned baldness occurs in women, though it progresses more slowly and does not reach the end stage of complete denudation. An effective treatment for these and other related conditions has long been sought.

Many women think thinning hair is abnormal or unnatural, i.e., a man's problem. Some believe that if their hair is thinning, then they must be sick, or that it's stress related. Among women younger than 50 who experience hair thinning, most assume that it is caused by something external, while women over 50 normally attribute it to just another part of aging. Temporary conditions such as pregnancy, medication, diet, or stress can cause hair thinning. However, for 70% of the women who experience the condition, it can be attributed to androgenic alopecia.

Both women and men experience androgenic alopecia and approximately 50 million men have hereditary hair thinning compared to nearly 30 million women. However, it affects the genders differently. While men experience "pattern baldness", vertex balding and/or receding frontal hairline, women generally experience diffused thinning over the top of the head or crown, while most often maintaining a frontal hairline. Androgenic alopecia is non-discriminating, affecting men and women of all races and ethnicities, and is a genetically inherited condition.

Surprisingly, it is not something that happens to women only after menopause. It can begin as early as the 20s and is so common, that by age 35, almost 40% of women demonstrate some signs of hair thinning. By the age of 50, approximately 50% of women will experience some degree of hair-thinning.

As one ages, a combination of heredity, the effects of hormones and age causes certain hair follicles to get smaller and smaller. This prevents the hair from fulfilling its regular growth process, which is usually ½ inch per month. With androgenic alopecia, genetically predisposed follicles gradually become smaller and the period of time in which the hair grows is reduced—a process known as miniaturization. And hair that can only grow for a short time is shorter, thinner, even colorless.

There are two types of hair follicles which produce either "terminal hairs" or "vellus hairs." Terminal hairs are coarse, pigmented, long hairs in which the bulb of the follicle is situated deep in the skin, usually in the subcutaneous tissue. Vellus hairs, on the other hand, are fine, thin, non-pigmented short hairs whose bulbs are located superficially in the upper dermis. In patterned alopecia, follicles which produce terminal hairs are gradually converted to vellus ones through a miniaturization process.

Along with this progressive involution there inevitably occurs changes in the proportion of hairs in the various phases of the hair cycle. All follicles pass through a life cycle that includes three phases namely, (1) anagen (2) catagen and (3) telogen. The anagen phase is the period of active hair growth on the scalp that generally lasts from 3–6 years. Catagen is a short transitional phase when the follicle contracts in preparation for a resting period. It lasts a couple of weeks. In the telogen phase, the follicle is in a resting phase where all growth ceases and the hair becomes consisted of short "club" hairs. When a new cycle begins, the club hair is shed. Telogen scalp hairs are relative short-lived, and last only about three to four months.

Normally, approximately 90% of scalp hairs are in the anagen phase, less than 1% exist in the catagen phase and the remainder are in the telogen phase. With the onset of patterned baldness, a successively greater proportion of hairs are in the telogen phase, with correspondingly fewer in the active growth anagen phase.

Additionally, there may be some actual loss of hair follicles but this is limited to the last final phase. For the most part, the visible diminution in the bulk of hair is due to the miniaturization of the follicles. In completely bald areas, all the follicles are in the vellus phase producing ugly, fine, short, non-pigmented hairs which are cosmetically useless. It may take 20 to 30 years for the distinctly anagen follicles on the crown to become transformed into a uniform population of vellus follicles.

Patterned baldness is sometimes called androgenic alopecia because male hormones are necessary for its development. It does not occur before adolescence, nor in castrates.

Attempts to prevent alopecia by hormonal treatments by using anti-androgens or female hormones have failed. A hereditary component is also recognized since patterned alopecia runs in families. Despite intensive investigation, the mechanism whereby terminal follicles convert to vellus ones is unknown.

At the present time, one effective surgical treatment for patterned alopecia is hair transplantation. Plugs of hair-bearing skin from the back of the scalp are transplanted into the bald areas. The procedure is costly and painful. Hundreds of plugs must be transplanted to create an appearance of hairiness and it is virtually impossible to obtain anything near the original density and thickness of terminal hair.

Many other approaches for creating or reversing patterned alopecia have been tried including ultra-violet radiation, massage, chemical irritation and innumerable natural products and herbs. However, none of these have been generally accepted as effective.

It is an object of the present invention to provide a method and means for measuring the degree and rate of hair loss in a given individual, and in particular, in women. The device and method not only are useful in determining how much hair is lost, but, when used in conjunction with the therapies discussed above, how much hair may be regained through the stimulation of new growth and/or the rate at which such hair loss may be delayed and/or retarded.

Pharmaceuticals offer a more rational approach although most tested have been found to be poorly metabolized and the results have been less than satisfactory. In Europe, a schedule of estrogens and anti-androgens have been administered orally to balding females with inconsistent results and with obvious limitations.

The topical application of minoxidil is currently the most effective therapy for patterned alopecia. Minoxidil is a well-known pharmaceutical agent marketed by the Pharmacia Corporation (Peapack, N.J.) and administered in tablet form for the treatment of hypertension. Numerous investigators have demonstrated that it can also stimulate visible hair growth in a majority of balding subjects. The structure and use of this compound is described in U.S. Pat. Nos. 4,139,619 and 4,596,812 to Chidsey, et al. This compound has varying degrees of efficacy for moderating androgenic alopecia, depending on the degree of baldness, its duration, the age of the patient and, of course, on the concentration of the drug in an appropriate vehicle. Early detection of hair loss and treatment with minoxidil can retard further hair loss and stimulate re-growth thereby preventing baldness to a greater extent. Therefore, the earlier it is detected, the better are the chances for hair loss prevention.

The ability to diagnose hair loss in its earliest stages is difficult however and compounded by many aesthetic factors which reflect the visual contrast between hair color and character against the color background of the scalp. In individuals with black course hair and white skin, the contrast is dramatic and hair loss is evident early in the process. In individuals with blond hair and blond skin, significant hair loss can occur before it is evident as the contrast between scalp and hair color is minimal.

In a somewhat related invention, U.S. Pat. No. 6,253,771 to McClaine discloses and claims a comb-like device that is useful in the measurement of hair thickness and density in order to determine the extent and/or degree of hair loss or thinning as well as hair regeneration if undergoing treatment therefore. The comb section or teeth are modified into a plurality of different sized tines for measuring hair depth and thickness while the handle is tapered and calibrated for measuring any increase or decrease in the size of the individual's part. The handle is further modified through the incorporation of a magnifying glass for visual inspection of the individual's hair and scalp. The device is primarily designed for women but is used by hair stylists or dermatologists and not the individual to determine the extent of hair density change.

SUMMARY OF THE INVENTION

The hair density self-analysis device of the present invention allows for the individual to measure the amount of hair or lack thereof on his or her head without the need for assistance from others. Primarily designed for use by women, the device measures two parameters, the width of the midline part in the scalp and the thickness or density of the ponytail. The device is comprised of a head or body portion that houses an adjustable gauge with operatively connected tines for measuring the part and a flexible handle or appendage portion that is calibrated and measures the thickness and density of the ponytail.

DETAILED DESCRIPTION OF THE DRAWINGS

DETAILED DESCRIPTION OF THE INVENTION

U.S. Pat. No. 4,596,812, to Chidsey, et al., discloses the use of minoxidil (6-amino-1,2-dihydro-1-hydroxy-2-imino-4-piperidinopynrmidine), as a therapeutic agent to treat alopecia and arrest and reverse male pattern alopecia. U.S. Pat. No. 4,139,619, also to Chidsey, discloses the use of minoxidil and related 6-amino-4(substituted amino)-1,2-dihydro-1-hydroxy-2-imino-pyrimidines as a means for (a) increasing the rate of growth of terminal hair, and (b) converting vellus hair to grow as terminal hair. U.S. Pat. No. 5,026,691 to Klegman discloses and claims pharmaceutical compositions comprising minoxidil in combination with anti-inflammatory agents for treating human baldness. The use of retinoids alone or in combination with minoxidil and related substituted pyrimidines to increase hair growth is disclosed in PCT publication numbers PCT/US85/04577, PCT/US83/02558 and PCT/US82/02833. The use of minoxidil sulfate (2,6,-diamino-4-piperidinyl)-1-(sulfooxy)-pyrimidinium hydroxide) as a therapeutic agent to stimulate hair growth is disclosed in PCT Application PCT/US86/00073 published Jul. 31, 1986. All of these patents and applications (when issued) are hereby incorporated by reference.

The self-analysis hair density device of the present invention consists of a body or housing portion that comprises an adjustable gauge that is operatively connected to a set of prongs or tines which widen or narrow in response to the manual adjustment of the gauge by the individual user. Preferably, the set of tines consists of three prongs with one central tine or prong affixed in an immovable position with respect to the other two. Using a mirror, the individual places the tips of the tines against the midline part and using the turnable dial affixed to the housing and operatively attached to the tines, adjusts them to match the width of the part. The adjustable dial is calibrated in millimeters so that once the tines are matched to the distance of the width of the part, the gauge can be read to indicate just how wide the part actually is.

At the end of the housing opposite to that from which the moveable tines or prongs extend is a flexible, tapered handle or flange that is calibrated from 0–10 centimeters. The individual user can wrap this about his or her ponytail or move and measure the circumference thereof. This is done by wrapping the handle around the ponytail and inserting the end or tip of the handle through a slot or grooved notch in the base of the body or housing wherefrom the tapered handle extends. The handle is tightened about the circumference of the ponytail and then slipped off the end whereby the measurement on the handle can be read.

Figure 1:
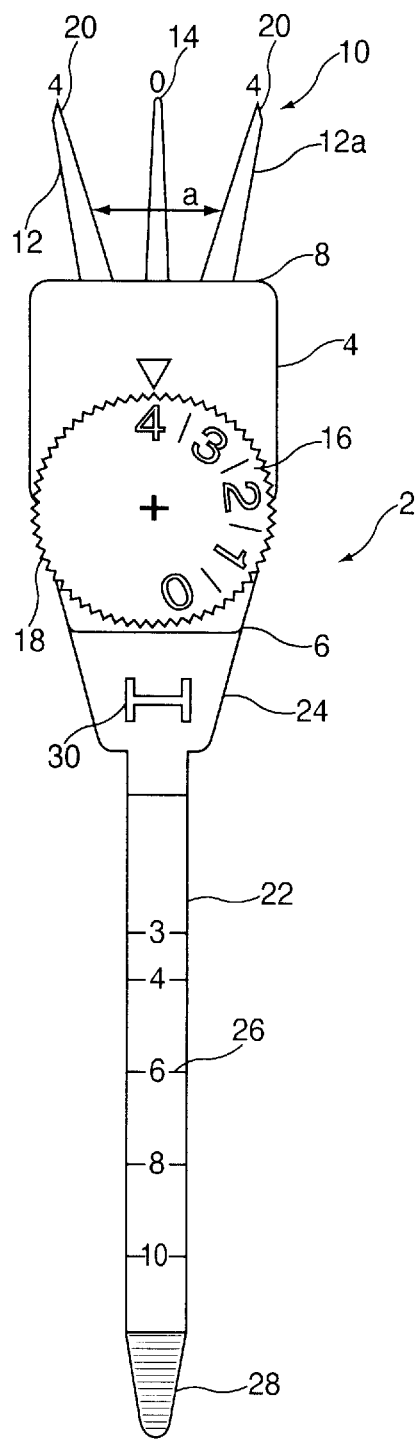
FIG. 1 is an overall top view of a first embodiment of the present invention.

Referring now to FIG. 1, the present invention (2) consists of a substantially rectangular housing or body (4) which may be tapered at the handle or distal end (6) as shown or more squared as in a standard four-sided rectangle. At the proximal end of the housing (8), a set of prongs or tines (10) extends out from the housing and these are also preferably tapered as shown. Whereas only two movable tines are necessary in the practice of the present invention, the set most preferably consists of three (3) prongs or tines with two (2) outer movable tines (12, 12a) and one (1) central fixed and immovable tine (14). And, whereas there is no standard size necessary for the housing and tines which can be manufactured according to specification, generally the housing body will be three (3) to four (4) inches in length, and one-half (½) to three-quarters (¾) inches in thickness. The tines or prongs are about two (2) to three (3) inches in length and two (2) to four (4) millimeters thick.

Although all three tines extend into the housing body (4), only two tines (12, 12a) are moveable and are operatively connected to the adjustable gauge (16) by means of a gear or pivot mechanism (not shown) housed therein. The gear or pivot mechanism is known in the art and operates whereby circular rotation of the circular gauge (16) rotates a cam which in turn rotates a gear or moves the pivot which widens or closes the width between the tines (12, 12a).

In FIG. 1, the gauge consists of a substantially circular disk or dial with serrated or groove edges (18) to allow the individual user to readily turn or rotate the gauge about its central axis. As can also be seen from FIG. 1, the gauge is calibrated about approximately one-half of its circumference with numbers measuring 0–5 millimeters.

Although not shown in the Figures, within the housing body there is a gear or pivot mechanism as is known in the art such that the adjustable gauge (16) is operatively connected to the moveable tines (12, 12a). By manually turning the:circular gauge (16), the gear mechanism moves the tines such that the distance (a) between them widens or narrows. As depicted, turning the gauge to a reading of 0 mm narrows the space between the tines while turning it to 4.0 mm widens it.

Using a mirror, the individual places the tips (20) of the tines (12, 12a) against the scalp at the midline part. The circular, calibrated gauge (16) is then turned by the individual user moving the tines until the two bridge the width of the users part. The gauge then, can be read, indicating the width of the part in millimeters and thereby, over time, can show whether or not the width of the part is expanding, an indicia of hair loss, or contracting, an indicia of re-growth and/or regeneration.

Figure 2:
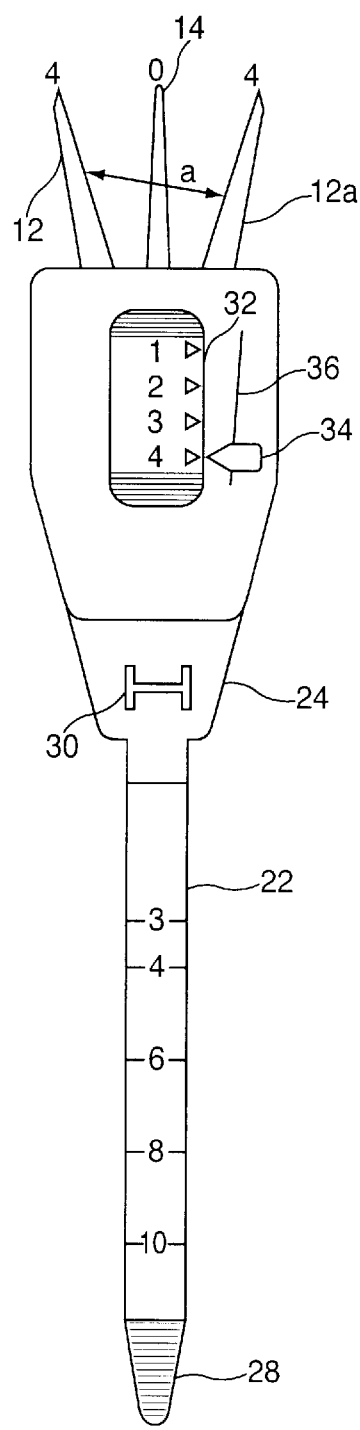
FIG. 2 is an overall top view of a second embodiment of the present invention.

Referring now to both FIGS. 1 and 2, the self-analysis hair density device of the present invention further comprises a flexible handle or flange (22) that extends from the distal end (24) of the housing body (4) opposite to that the proximal end (8) from which the tines (12, 12a and 14) extend. The handle (22) is calibrated along its length from 0–10 centimeters (26) and is tapered at its most distal end (28). Opposite thereto, within the distal end (24) of the housing body (4), a slot or grooved notch (30) extends through the tapered-distal end (24) which may also be flexible in design.

The tapered, flexible handle (22) is operated by the user by wrapping it around his or her ponytail or mane. The tapered end (28) of the handle (22) is pulled around the ponytail and inserted into and through the slot (30). The handle (22) is then tightened, like a noose, about the ponytail to measure its density. The noose is then slipped off the ponytail and the number on the handle (22) which is aligned with the edge of the slot (30) indicates the circumference of the ponytail that directly correlates with hair density.

Referring now to FIG. 2, a second embodiment of the present invention is shown comprising a variation of the gauge element (16). Here, the gauge is comprised of calibrated indicia (32) arranged along the central longitudinal axis of the housing body (4). The indicia are immovably affixed to the housing body (4) and are calibrated from preferably 0 to 5.0 millimeters, as in FIG. 1. Juxtaposed to said indicia is a movable pointer-tip (34) which is longitudinally aligned with the indicia on the right side as shown. Whether the tip pointer (34) is aligned with the calibrated indicia on the left side or the right side is immaterial and either alignment is satisfactory for purposes of the present invention so long as the calibrated indicia (32) are arranged accordingly.

As with the device depicted in FIG. 1, the pointer tip (34) is operatively connected to the moveable tines (12, 12a) such that movement of the pointer tip (34) along a second slot (36) longitudinally disposed within the housing body (4) widens or narrows the distance between the moveable prongs or tines (12, 12a). The pointer tip (34) is operatively connected to the moveable tines with a gear or pivot mechanism (not shown) in the housing body (4) as is known in the art and similar to that incorporated in the device of FIG. 1. As such, movement of the pointer tip (34) as shown in an upward direction towards the 1.0 mm marking will narrow the distance (a), between the moveable tines (12, 12a) while moving it in a downward direction as shown towards a reading of 4.0 mm will widen the distance (a) between the tines (12, 12a).

The tines or prongs (12) are placed against the users scalp and used to measure its width as described with respect to the operative embodiment depicted in FIG. 1. The flexible handle (22) with its tapered tip (28) is also used to measure the density of the individual users ponytail or mane as hereinbefore described. The device can be manufactured out of a variety of materials as is known in the art although a polyethylene or polypropylene plastic is preferred based on economy of the materials and weight of the finished product.

What I claim is:

1. A self-analysis hair density measuring device comprising:
   a) a housing body;
   b) a calibrated gauge element movably affixed to one side of said housing body;
   c) at least two movable pronged tines extending from within a proximal end of said housing body;
   d) a gear or pivot mechanism disposed within said housing body operatively connecting said tines with said gauge and,
   e) a flexible handle extending from an the distal end of said housing body that is numerically calibrated with a tapered distal tip.

2. The hair density device of claim 1 wherein manual movement of the calibrated gauge element widens or narrows the distance between the two moveable tines.

3. The hair density device of claim 2 further comprising an affixed, immovable tine centrally disposed between the two outer movable tines.

4. The hair density device of claim 1 wherein said housing body further comprises a grooved slot extending through a portion of its distal end.

5. The self-analysis hair device of claim 4 wherein said tapered tip of the flexible handle can be folded around an ponytail of a user of the device and inserted through the grooved slot disposed in the distal end of the housing body.

6. The hair density-measuring device of claim 5 wherein said gauge is comprised of a substantially circular calibrated disk.

7. The hair density-measuring device of claim 6 wherein the cirucmferential edge of said circular disk is serrated or uniformly grooved.

8. The hair density-measuring device of claim 5 wherein said gauge is comprised of calibrated indicia affixed to one side of said housing body along its longitudinal axis in juxtaposition to a slideably movably pointer tip.

9. The hair density device of claim 8 wherein said pointer tip is operatively connected to said movable tines by means of the gear or pivot mechanism disposed within said housing body.

10. A method for the self-analysis and measurement of the loss or re-growth of one's hair using the hair density measuring device of claim 1.

11. A method for the self analysis and measurement of the loss or re-growth of one's hair using the hair density measuring device of claim 1, comprising folding the tapered tip of the flexible handle around a ponytail of a user of the device and inserting the tip through the grooved slot in the distal end of the housing body, whereby hair density is directly indicated."

* * * * *